(12) United States Patent
Liu et al.

(10) Patent No.: US 11,458,476 B2
(45) Date of Patent: Oct. 4, 2022

(54) IN-SITU FECAL SPECIMEN SAMPLING DEVICE

(71) Applicant: Marvin Liu, Los Angeles, CA (US)

(72) Inventors: Marvin Liu, Los Angeles, CA (US); Bonnie Liu, Los Angeles, CA (US)

( * ) Notice: Subject to any disclaimer, the term of this patent is extended or adjusted under 35 U.S.C. 154(b) by 232 days.

(21) Appl. No.: 16/656,556

(22) Filed: Oct. 17, 2019

(65) Prior Publication Data

US 2021/0114015 A1 Apr. 22, 2021

(51) Int. Cl.
*B01L 3/00* (2006.01)

(52) U.S. Cl.
CPC ......... *B01L 3/505* (2013.01); *B01L 2300/042* (2013.01); *B01L 2300/0832* (2013.01); *B01L 2300/0851* (2013.01); *B01L 2300/123* (2013.01)

(58) Field of Classification Search
CPC ............... B01L 3/505; B01L 2300/042; B01L 2300/123; B01L 2300/0851; B01L 2300/0832; A61B 10/0096; A61B 10/0038
USPC ....................................................... 422/550
See application file for complete search history.

(56) References Cited

U.S. PATENT DOCUMENTS

| 2,349,962 | A | * | 5/1944 | Harris | B65D 35/02 222/541.2 |
| 3,456,850 | A | * | 7/1969 | Uhlmann | A47K 5/122 222/180 |
| 5,265,620 | A | | 11/1993 | Fisher | |
| 5,624,554 | A | * | 4/1997 | Faulkner | A61B 10/0038 210/232 |
| 2004/0082878 | A1 | * | 4/2004 | Baldwin | B01L 3/5029 600/573 |
| 2016/0139164 | A1 | * | 5/2016 | Brueckner | G01N 35/1009 436/501 |

FOREIGN PATENT DOCUMENTS

| CN | 105092283 A | | 11/2015 |
| CN | 105092292 B | | 7/2018 |
| CN | 208383478 | * | 1/2019 |
| WO | 2008089198 A1 | | 7/2008 |
| WO | 2012088330 A2 | | 6/2012 |

* cited by examiner

*Primary Examiner* — Benjamin R Whatley
*Assistant Examiner* — Jacqueline Brazin (57) ABSTRACT

An in-situ fecal specimen sampling device for stool tests, comprising: a sampling tube of a tube-like structure comprising an bottom with an opening; a sampling structure disposed inside the sampling tube is attached to the bottom of the sampling tube, and is an tube-like structure with a closed top end, an bottom end with opening and an stretchable soft body, which can insert a finger from the opening of the bottom outside the sampling tube and push forward and stretch the closed top end to beyond the sampling tube. The sample provider is able to collect the sample by placing the sampling structure onto the stool or inside the anus through the finger operated sampling structure by himself. All of the process can be finished during defecation process in-situ.

8 Claims, 11 Drawing Sheets

IN-SITU FECAL SPECIMEN SAMPLING DEVICE

TECHNICAL FIELD

The present invention relates to the field of fecal specimen sampling devices and in particular to an in-situ fecal specimen sampling device.

BACKGROUND OF THE INVENTION

Stool tests are one of the routine clinical laboratory examinations. It is very important test for early screening of many diseases. Visual examination includes color and texture/consistency—formed. Screening includes fecal occult blood test, or fecal immunochemical test, fecal DNA test. Microbiology tests include parasite for worm larvae or eggs and stool culture for bacteria. Chemical tests include fecal pH, fecal fat, and fecal elastase. Microscopic examination is used to find out if there are over-numbered white blood cells, red blood cells, and macrophages. Therefore the sampling of feces is the first step for stool tests. Currently, the sampling devices to collect stool samples use a swab or spoon-shaped sampling head after stool on toilet so it is not convenient and not free from contamination because the toilet has small amount of resident water inside. There has been no way to collect the stool samples in-situ during normal defecation process using the current sampling devices. There are many patent disclosures, such as WO2012/088330A2, U.S. Ser. No. 00/526,5620A, WO2008/089198A2, CN105092292B and CN105092283A, but all of them are to collect the samples after stool and have no in-situ sampling function. Therefore, it is important to develop in-situ fecal sampling device for stool tests.

SUMMARY

It is the object of the present invention to provide a fecal specimen sampling device to collect the stool samples in-situ during the normal defecation process.

The present invention provides an in-situ fecal specimen sampling device for stool tests, comprising:

a sampling tube of a tube-like structure comprising an bottom with an opening;

a sampling structure disposed inside the sampling tube is attached to the bottom of the sampling tube, and is an tube-like structure with a closed top end, an bottom end with opening and an stretchable soft body, which can insert a finger from the opening of the bottom outside the sampling tube and push forward and stretch the closed top end to beyond the sampling tube.

The in-situ fecal specimen sampling device includes the sampling tube, the sampling structure, a sampling head, a sampling tube cap, wherein:

the sampling tube of the tube-like structure comprising the bottom with an opening and an opened top;

the sampling structure disposed inside the sampling tube is attached and sealed by the opening of the sampling tube to the opening of the sampling structure, the sampling structure is a tube-like structure with a closed top, an open bottom, and a tubing body that is stretchable and soft, in which can insert a finger from the opening of the bottom outside the sampling tube and push forward and stretch the closed top end to beyond the sampling tube, and the top end of the sampling structure is a closed end with a sampling head;

the opening of the sampling structure for finger insertion is disposed on the bottom of the sampling tube from outside;

the top end of the sampling head has a sample collecting structure;

the top of the sampling tube is provided with a removable sampling tube cap.

The sampling device comprises a sampling tube cap, a rod-like structure is provided on the inner side of the sampling tube cap to push a sampling head of the sampling structure back into the sampling tube.

The sampling tube comprises a compressible structure.

The sampling head is a closed end structure with at least one of a claw, a ring, a flat and a spoon-shaped structure.

The sampling structure comprises a top, a body and a bottom, wherein the body comprises an elastic telescopic structure and the bottom comprises the elastic contracted structure.

The sampling device also includes a sampling glove and during application, the sampling glove is worn and the glove protected finger is inserted into the sampling structure for operation.

The sampling tube is a tube-like structure comprising an opened top and the bottom with an opening, and has a width of diameter 1.5 cm-5.0 cm and a height of length 1.0 cm-6.0 cm, and the sampling structure disposed inside the sampling tube is an soft tubular structure made of latex and has the inner diameter of the soft tubular structure of 1.5 cm-2.5 cm, wherein the top of the sampling structure is a closed end structure with a sampling head which comprises at least one of the characteristics as a claw, a ring, a flat and a spoon-shaped structure, the finger entrance at the bottom of the sampling tube is the opening on the bottom from outside and attached surround by the opening bottom of the sampling structure; wherein the top of the sampling tube is provided with a removable sampling tube cap with spiral buckle, and the inner side of the sampling tube cap is provided with a rod-like structure, and the rod-like structure has a length of 0.5 cm-3.0 cm.

The sampling tube is a compressible tube-like structure comprising an opened top and the bottom with an opening, and has a width of diameter 1.5 cm-5.0 cm and a height of length 1.0 cm-6.0 cm, and the sampling structure disposed inside the sampling tube is an soft tubular structure made of latex and has an inner diameter of 1.5 cm-2.5 cm, wherein the top of the sampling structure is a closed end structure with a sampling head which comprises at least one of the characteristics as a claw, a ring, a flat and a spoon-shaped structure, the finger entrance at the bottom of the sampling tube is the opening on the bottom from outside and attached surround by the opening bottom of the sampling structure; wherein the top of the sampling tube is provided with a removable sampling tube cap with spiral buckle, and the inner side of the sampling tube cap is provided with a rod-like structure, and the rod-like structure has a length of 0.5 cm-3.0 cm.

The present disclosure provides the application of the in-situ fecal specimen sampling device in the development of fecal specimen sampling device.

The present disclosure has following advantages due to the above technical solutions:

This invention utilizes the design that the sampling structure disposed inside the sampling tube is a retractable structure, and a finger can insert into the sampling structure for samples collection. Furthermore, the sampling structure inside the sampling tube is a full closed and isolated and has glove worn for further protection, and it can prevent any contamination in both the samples and the hand. So the sample provider is able to collect the sample by placing the sampling head onto the stool or inside the anus through the finger operated sampling structure by himself. All of the process can be finished during defecation process in-situ.

In this invention, the sampling tube cap and the rod-like structure are used in the collecting process; the samples collected can be stored without any contamination and can add test reagents when it is ready for use.

In this invention, the sampling tube is a retractable compression structure, which ensures that the sampling tube can be compressed and does not affect the sample collecting process. When the sampling tube is not in operation, the compressed sampling tube can be stretched to extension state, and the test reagents can be added without affecting the testing process.

In this invention, the sampling structure comprises an elastic contracted structure on the bottom, which allows the bottom of the sampling structure to tighten to the lower portion of the finger and has the body portion of the sampling structure stretched longer to beyond the sampling tube for sample collection.

DETAILED DESCRIPTION OF EMBODIMENTS

This invention will be described in detail below with reference to the accompanying drawings and embodiments, but these embodiments are not intended to limit the invention.

Figure 1:
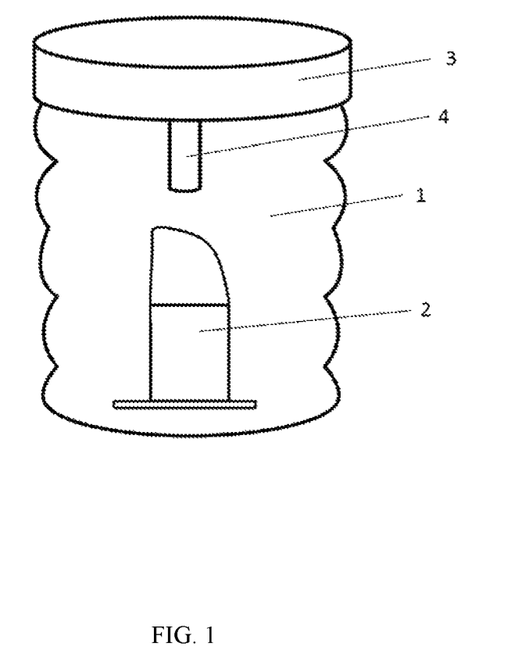
FIG. 1 is a schematic diagram of the overall design of this invention with compressible sampling tube.
Figure 3:
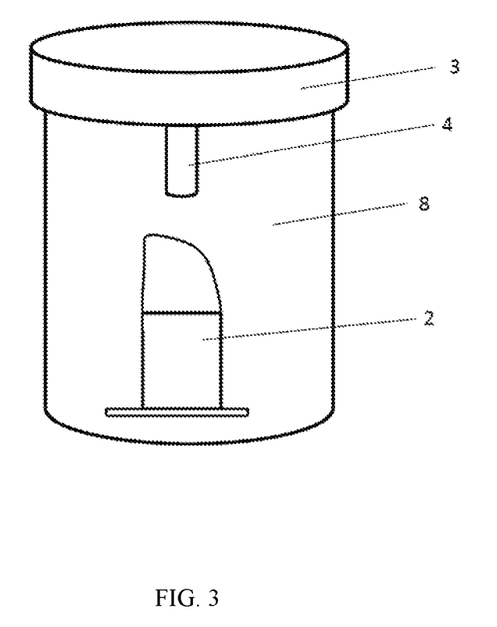
FIG. 3 is a schematic diagram of the overall design of this invention with incompressible sampling tube.

As shown in FIG. 1, FIG. 3, the structure of the invention for in-situ fecal specimen sampling device includes an sampling tube 1, a sampling structure 2 inside the sampling tube 1, a sampling tube cap 3 at the top of the sampling tube 1 with spiral buckle and a rod-like structure 4 attached to the inner side of the sampling tube cap 3. The sampling structure 2 is a hollow tube-like structure with an opening at the bottom and a closed end at the top. The sampling structure 2 is attached and sealed to the opening on the bottom of the sampling tube 1. While in the application, it need to remove the sampling tube cap 3 first and then can expose the sampling structure 2. The sampling tube 1 includes a compressible and stretchable structure 1 and a flat and incompressible structure 8.

Figure 2:
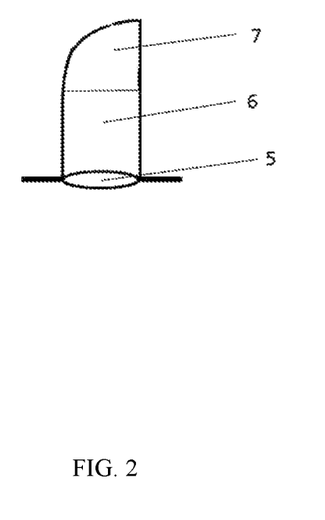
FIG. 2 is a schematic diagram of the sampling structure.

As shown in FIG. 1 and FIG. 2, the sampling structure 2 of this invention is a hollow tube-like structure with an opening at the bottom and a closed end at the top, including a lower portion 5 (the bottom with an opening), a body portion 6 (the tubing body in stretchable and soft) and a head portion 7 (the closed top). The lower portion 5 is attached to the bottom of the sampling tube 1. The body portion 6 is an elastic structure and is compressible and stretchable. The head portion 7 provides a collecting structure with a claw, spoon, flat or ring-shaped structure. The sampling structure 2 allows a finger to insert into the inside through the opening at the bottom of the sampling tube 1 and stretches to push the head portion 7 extend beyond the sampling tube 1. Because the body portion 6 is an elastic stretching structure, a finger can push and stretch it longer, so that the head portion 7 is able to extend to beyond the top opening of the sample tube 1 for sample collection.

Figure 4:
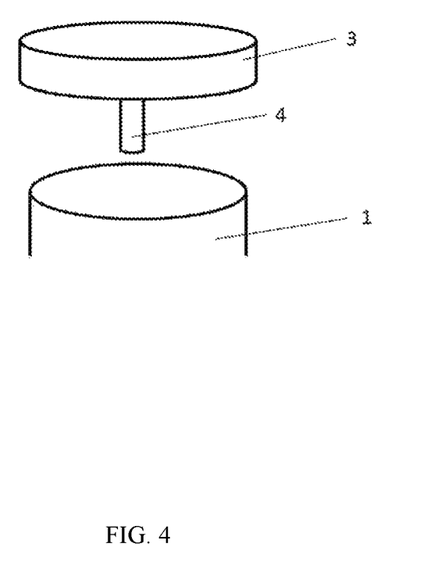
FIG. 4 is a schematic diagram of the sampling tube cap.
Figure 5:
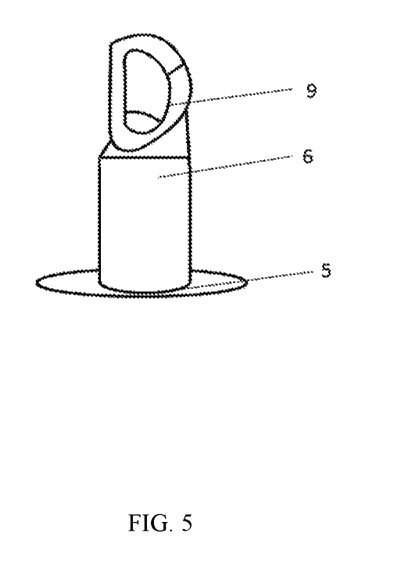
FIG. 5 is a schematic diagram of the sampling head with a spoon-shaped.
Figure 6:
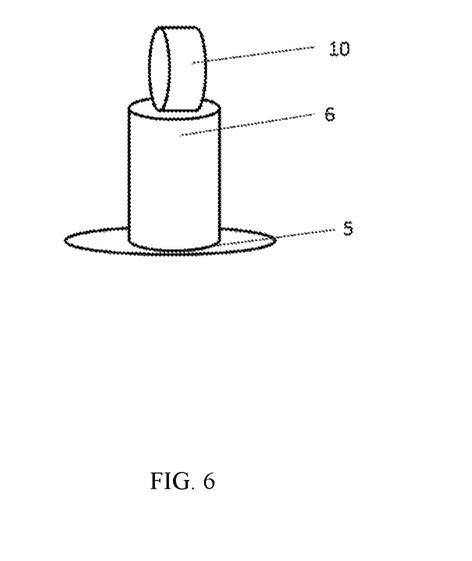
FIG. 6 is a schematic diagram of the sampling head with a ring-shaped.
Figure 7:
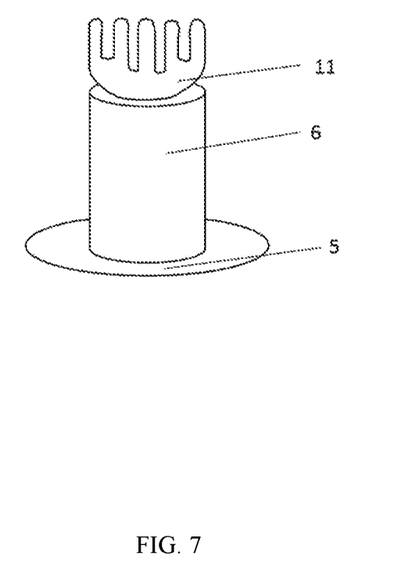
FIG. 7 is a schematic diagram of the sampling head with a claw-shaped.
Figure 8:
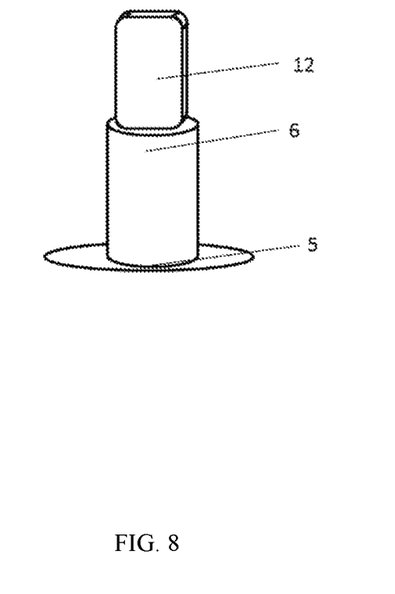
FIG. 8 is a schematic diagram of the sampling head with a flat-shaped.

As shown in FIG. 1 and FIG. 4, the sampling structure cap 3 of this invention is provided with a rod-like structure 4 on the inner side, which is able to push the head portion 7 back into the sampling tube 1 after sample collection.

As shown in FIG. 1 and FIGS. 5-8, the sampling head 7 has a collecting structure at the closed end of the top of the sampling structure 2 as spoon-shaped structure 9, ring-shaped structure 10, claw-shaped structure 11 and flat-shaped structure 12.

Figure 9:
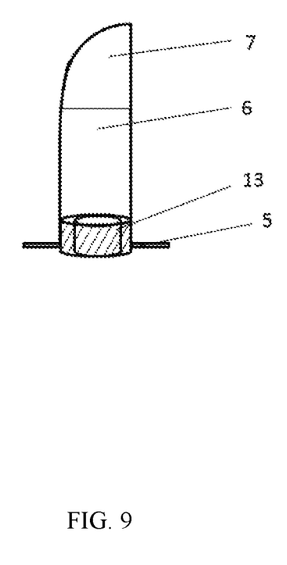
FIG. 9 is a schematic diagram of the sampling structure with a contracted bottom.

As shown in FIG. 1 and FIG. 9, the sampling structure 2 includes a lower portion 5, a body portion 6 and a head portion 7. Wherein an elastic contracted rounding structure 12 is provided at the lower portion 5 of the sampling structure 2, which allows the bottom of the sampling structure 2 tighten to the lower portion 5 of the finger and has the body portion 6 of the sampling structure 2 stretched longer to beyond the sampling tube 1 for sample collection.

Figure 10:
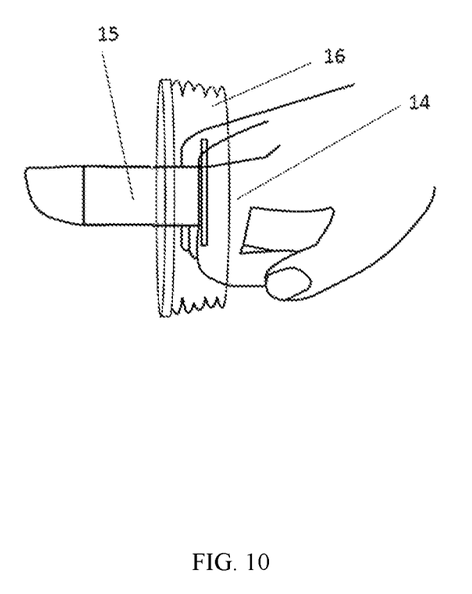
FIG. 10 is a schematic diagram of the operation status of the design with compressible sampling tube.

As shown in FIG. 1 and FIG. 10, for the operation using the compressible sampling tube 1, compress the compressible sampling tube 1 into a compressed state 16, insert the finger 14 into the sampling structure 2, push and stretch the sampling structure 2 into a sampling collecting state 15 to beyond the opening of the sampling tube as a compressed state 16 and perform sample collection. After collection, pullout the finger 14 from the sample structure 2, take the sampling tube cap 3, push the sampling head 7 into the sampling tube 1 using the rod-like structure 4 and cover the sampling tube with the sampling tube cap 3, so that the sampling structure 2 is retracted to the compressible sampling tube 1, the compressible sampling tube 1 is restored to its original state, and the fecal sample collection is finished.

Figure 11:
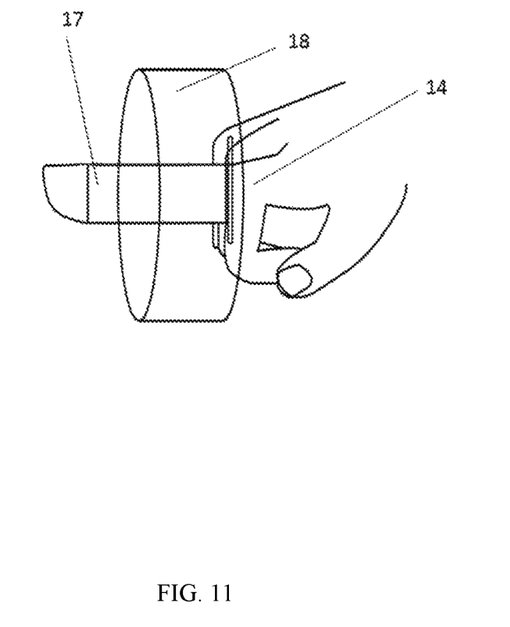
FIG. 11 is a schematic diagram of the operation status of the design with incompressible sampling tube.

As shown in FIG. 3 and FIG. 11, the operation of using the incompressible sampling tube 8 allows for the user to insert the finger 14 into the sampling structure 2, push and stretch the sampling structure 2 into a sampling collecting state 17 to beyond the opening of the sampling tube 18 and perform sample collection. After collection, pullout the finger 14 from the sample structure 2, take the sampling tube cap 3, push the sampling head 7 into the sampling tube 8 using the rod-like structure 4 and cover the sampling tube 1 with the sampling tube cap 3, so that the sampling structure 2 is retracted to the incompressible sampling tube 8, the incompressible sampling tube 8 is restored to its original state, and the fecal sample collection is finished.

The performance of the invention will be further illustrated with reference to specific experiments.

The experimental materials included 2 cm high incompressible plastic bottles with cap, 3 cm high compressible plastic bottles with caps, a plastic claw, a latex glove, a plastic rod.

The experimental device was prepared as follows. Open a hole 1.5 cm in diameter at the bottom of the two kind of plastic bottles. Cut the finger portion of latex glove and was used for the sampling structure. A plastic claw is glued on the fingertip. The finger with the plastic claw is put into the plastic bottle from the opening at the bottom of the plastic bottle, and then it is sealed and pasted to the bottom of the plastic bottle with glue. Glued and attached a 1 cm long plastic rod to the inner side of the plastic bottle cap. The experimental model of this invention was prepared.

The experimental method and results are described as follows. Removed the plastic cap, inserted the finger from the opening at the bottom of the plastic bottle to the finger of the latex glove, pushed forward the finger to the fingertip beyond the opening of the plastic bottle, performed in-situ sample collection, then pulled out the finger, pushed the sampling head into the plastic bottle with a plastic rod, and covered the cap, put test reagents into the plastic bottle, and mixed for further testing. We had done total 100 collections and tests, all of the results were satisfied for the corresponding testing. The experiment was finished.

These embodiments are merely illustrative of the invention, and various changes can be made to the invention with respect to the structure and connection of the components. Equivalent changes and modifications made based on the content of the invention should fall within the scope of the invention.

What is claimed is:

1. An in-situ fecal sampling device for stool tests, comprising:
   a sampling tube comprising a bottom with a first opening; and
   a sampling structure disposed inside the sampling tube, wherein the sampling structure is attached to the bottom of the sampling tube, and the sampling structure comprises a closed top end, a bottom end with a second opening and a stretchable soft body, in which a finger is allowed to be inserted from the second opening of the bottom outside the sampling tube to push forward and stretch the closed top end of the sampling structure to beyond the sampling tube; and the first opening is overlain with the second opening, and has the same size with the second opening.

2. The device of claim 1, wherein: the closed top end of the sampling structure is provided with a sampling head; a top end of the sampling head has a sample collecting structure; and
   a top of the sampling tube is provided with a removable sampling tube cap.

3. The device of claim 2, wherein a rod structure is provided on an inner side of the removable sampling tube cap to push the sampling head of the sampling structure back into the sampling tube.

4. The device of claim 1, wherein the sampling tube comprises a compressible structure.

5. The device of claim 2, wherein the sampling head has at least one of a claw, a ring, a flat and a spoon-shaped structure.

6. The device of claim 1, wherein the sampling structure comprises a top, a body and a bottom, wherein the body comprises an elastic telescopic structure and the bottom comprises an elastic contracted structure.

7. The device of claim 2, wherein the sampling tube is a tube structure comprising an opened top and the bottom with the first opening, and has a diameter of 1.5 cm-5.0 cm and a length of 1.0 cm-6.0 cm, and the sampling structure disposed inside the sampling tube is a soft tubular structure made of latex, and an inner diameter of the soft tubular structure is 1.5 cm-2.5 cm, wherein the sampling head comprises at least one of the characteristics as a claw, a ring, a flat and a spoon-shaped structure; wherein the removable sampling tube cap is provided with a spiral buckle, and an inner side of the removable sampling tube cap is provided with a rod-like structure, and the rod-like structure has a length of 0.5 cm-3.0 cm.

8. The device of claim 2, wherein the sampling tube is a compressible tube structure comprising an opened top and the bottom with the first opening, and has a diameter of 1.5 cm-5.0 cm and a length of 1.0 cm-6.0 cm, and the sampling structure disposed inside the sampling tube is a soft tubular structure made of latex and has an inner diameter of 1.5 cm-2.5 cm, wherein the sampling head comprises at least one of the characteristics as a claw, a ring, a flat and a spoon-shaped structure; wherein the top of the sampling tube is provided with the removable sampling tube cap with a spiral buckle, and an inner side of the removable sampling tube cap is provided with a rod-like structure, and the rod-like structure has a length of 0.5 cm-3.0 cm.

* * * * *